(12) United States Patent
Neading et al.

(10) Patent No.: US 6,515,194 B2
(45) Date of Patent: Feb. 4, 2003

(54) DIAPER HAVING CENTRALLY-LOCATED CHROMATOGRAPHIC LAYER WITH PERIPHERALLY-LOCATED WETNESS INDICATOR

(76) Inventors: Ryan R. Neading, 13688 Plaster Cir., Broomfield, CO (US) 80020; Ryan W. Cate, 6880 W. 61st Ct., #3201, Westminster, CO (US) 80021

( * ) Notice: Subject to any disclaimer, the term of this patent is extended or adjusted under 35 U.S.C. 154(b) by 38 days.

(21) Appl. No.: 09/742,515

(22) Filed: Dec. 20, 2000

(65) Prior Publication Data

US 2001/0049513 A1 Dec. 6, 2001

Related U.S. Application Data

(60) Provisional application No. 60/172,045, filed on Dec. 23, 1999.

(51) Int. Cl.[7] .................................................. A61F 13/15
(52) U.S. Cl. ................... 604/361; 604/375; 604/385.01
(58) Field of Search ................................. 604/361, 375; 128/886

(56) References Cited

U.S. PATENT DOCUMENTS

| | | | |
|---|---|---|---|
| 3,731,685 A | 5/1973 | Eidus ........................ 128/284 |
| 5,522,809 A | * 6/1996 | Larsonneur .................. 604/361 |
| 5,838,240 A | * 11/1998 | Johnson ...................... 340/604 |
| 5,947,943 A | 9/1999 | Lee ............................ 604/361 |
| 6,075,178 A | 6/2000 | La Wilhelm et al. ........ 604/361 |

* cited by examiner

Primary Examiner—Andy Falik
Assistant Examiner—Angela J Grayson
(74) Attorney, Agent, or Firm—Flanagan & Flanagan; John R. Flanagan

(57) ABSTRACT

A diaper includes a diaper substrate having a peripheral edge and a centrally-located region where fluid from a user will make initial contact therewith, a fluid transport layer disposed with the diaper substrate and having a peripheral edge and a centrally-located portion disposed at the centrally-located region of the diaper substrate, and a wetness indicator on the peripheral edge of the transport layer and exposed and extending along at least a portion of the peripheral edge of the diaper substrate. The transport layer made of a fluid-permeable chromatographic medium draws fluid via capillary action from its centrally-located portion at the centrally-located region of the diaper substrate toward its peripheral edge and into contact with the wetness indicator. The wetness indicator is a material capable of eliciting a visible response to the presence of fluid.

20 Claims, 3 Drawing Sheets

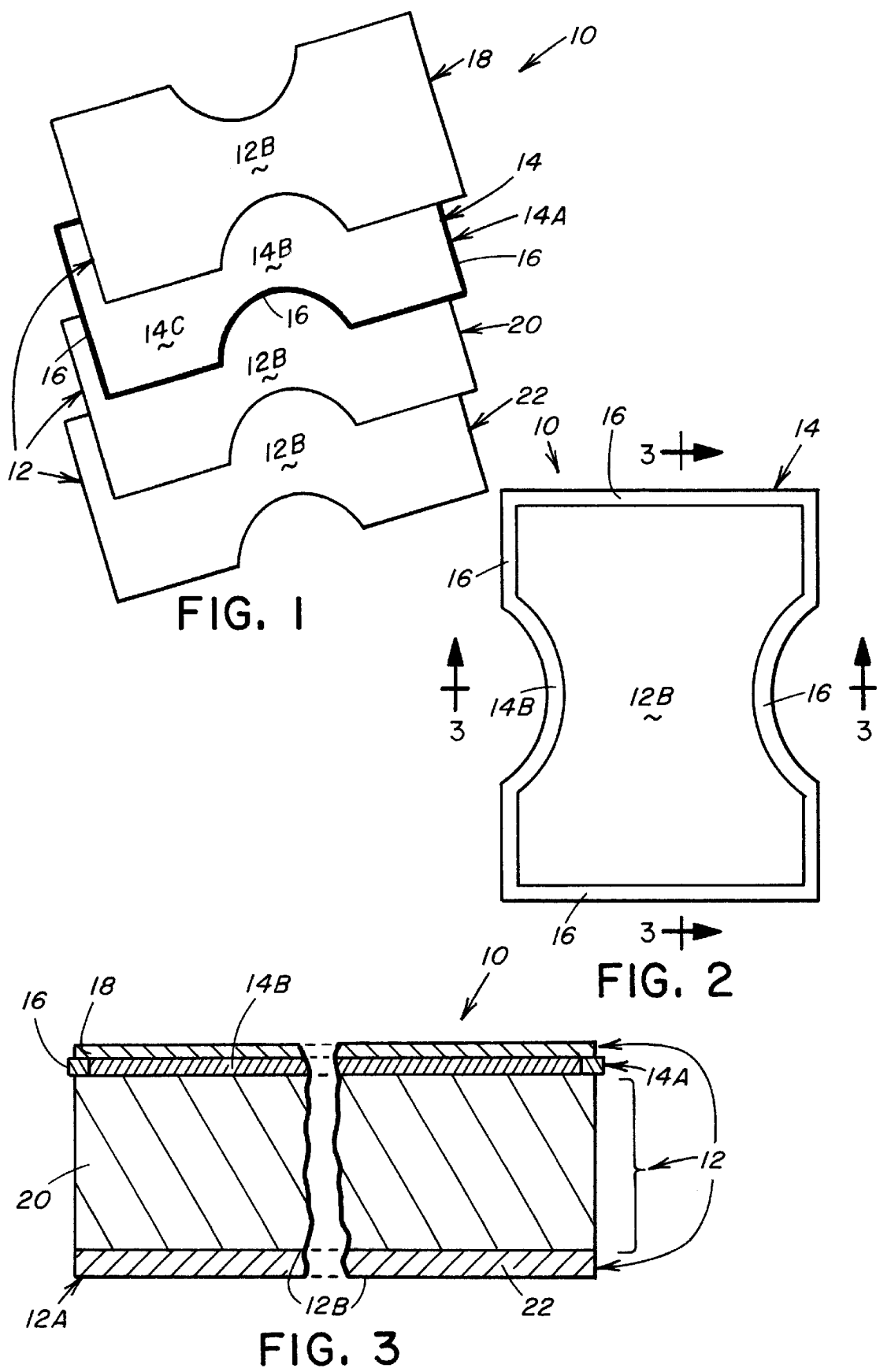

DIAPER HAVING CENTRALLY-LOCATED CHROMATOGRAPHIC LAYER WITH PERIPHERALLY-LOCATED WETNESS INDICATOR

This utility patent application claims the benefit of provisional application No. 60/172,045 filed Dec. 23, 1999.

BACKGROUND OF THE INVENTION

1. Field of the Invention

The present invention generally relates to diaper construction and, more particularly, is concerned with a diaper having a centrally-located layer of a fluid-permeable chromatographic medium with a peripherally-located wetness indicator.

2. Description of the Prior Art

A diaper is used on small children, infants and toddlers, to capture fluid and solid waste. When the diaper is wet or otherwise soiled from such waste, it is desirable and usually necessary to replace the diaper as soon as possible. A problem exists, however, in that it can be difficult to determine by touch whether a diaper on a child is wet or not because diapers generally have more than one layer and the outer layer is typically impermeable to the waste.

In order to provide a solution for this problem, wetness indicators for diapers have been developed over the years. Representative examples of prior art diaper wetness indicators are the ones disclosed in U.S. Pat. No. 3,731,685 to Eidus and U.S. Pat. No. 5,947,943 to Lee. In the Eidus patent, a diaper moisture indicating strip is disclosed for use in connection with a cloth diaper. One end of the Eidus diaper moisture indicating strip is attached to the cloth diaper near the periphery of the diaper and the other free end of the strip has a chemical which changes color when wet. The Eidus strip operates by capillary action. The Eidus strip, however, is dependent upon being attached at a substantially peripheral location on the diaper where fluid, such as urine, will not immediately directly contact the innermost end of the strip and thus the fluid will be delayed in reaching the moisture-indicating chemical on the outer end of the strip.

In the Lee patent, a wetness-indicating material is disposed on an interior-facing side of a back sheet of a diaper. The Lee wetness-indicating material changes its appearance after it is exposed to water. The Lee patent, however, appears to be unduly complex and costly for achieving this objective.

Consequently, a need still exists for an innovation in diaper construction which will provides an optimum solution for the problem of indicating wetness without introducing any new problems in place thereof.

SUMMARY OF THE INVENTION

The present invention provides a diaper which satisfies the aforementioned need. The diaper includes a layer of a fluid-permeable chromatographic medium which has a centrally-located portion and a peripherally-located wetness indicator. The layer is relatively simple and cost-effective in its construction. The diaper with such a layer operates in a comprehensive fashion in that it will respond to the presence of fluid at the centrally-located region of the diaper where fluid always makes its initial contact with the diaper.

Accordingly, the present invention is directed to a diaper which comprises: (a) a diaper substrate having a peripheral edge and a centrally-located region where fluid from a user will make initial contact therewith; (b) a fluid transport layer disposed within the diaper substrate and having a peripheral edge and a centrally-located portion disposed at the centrally-located region of the diaper substrate; and (c) a wetness indicator on the peripheral edge of the transport layer and exposed and extending along at least a portion of the peripheral edge of the diaper substrate; (d) the fluid transport layer being made of a fluid-permeable chromatographic medium capable of drawing fluid via capillary action from the centrally-located portion of the layer at the centrally-located region of the diaper substrate toward the peripheral edge of the layer and into contact with the wetness indicator, the wetness indicator being a material capable of eliciting a visible response in the presence of fluid.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is an exploded perspective view of a first embodiment of a diaper of the present invention.

FIG. 2 is a plan view of the diaper of FIG. 1.

FIG. 3 is an enlarged cross-sectional view of the diaper taken along either of longitudinal and transverse lines 3—3 of FIG. 2 or any other longitudinal or transverse line through the diaper.

DETAILED DESCRIPTION OF THE INVENTION

Figure 4:
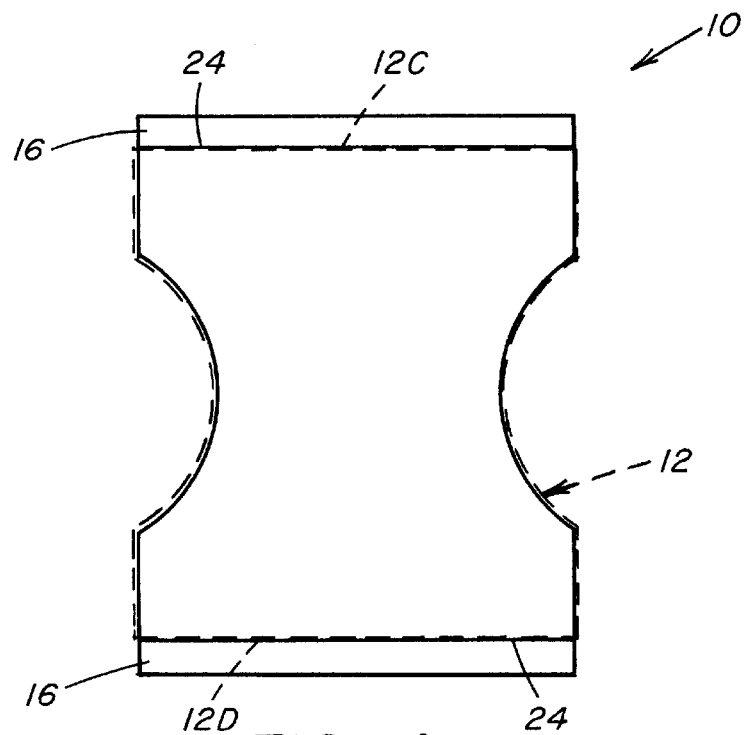
FIG. 4 is a plan view of a second embodiment of the diaper of the present invention shown in a dry condition.

Referring to the drawings and particularly to FIGS. 1 to 3, there is illustrated a first embodiment of a diaper, generally designated 10, of the present invention, preferably being a disposable diaper. The diaper 10 basically includes a diaper substrate 12, a fluid transport layer 14, and a wetness indicator 16. The diaper substrate 12 has a peripheral edge 12A and a centrally-located region 12B where fluid from a user will make initial contact with the diaper 10. The fluid transport layer 14 is integrated and disposed with the diaper substrate 12 and has a peripheral edge 14A and a centrally-located portion 14B disposed at the centrally-located region 12B of the diaper substrate 12. The wetness indicator 16 is provided on the peripheral edge 14A of the transport layer 14 and is exposed and extends along at least a portion of the peripheral edge 12A of the diaper substrate 12. The fluid transport layer 14 is, more particularly, made of a fluid-permeable chromatographic medium capable of drawing fluid via capillary action from the centrally-located portion 14B of the fluid transport layer 14 at the centrally-located region 12B of the diaper substrate 12 toward the peripheral edge 14A of the fluid transport layer 14 and into contact with the wetness indicator 16. The wetness indicator 16 is, more particularly, a material capable of eliciting a visible response, such as a color change of change in the size of a mark, in the presence of fluid.

The diaper substrate 12 basically can include an inner layer 18, an absorbent layer 20 and an outer layer 22 as are found in existing commercially-available disposable diapers. There also can be other combinations of layers. In the first embodiment, the layers 18, 20, 22 as are found in conventional diapers along with the fluid transport layer 14 provided by the present invention have configurations and sizes which are substantially the same. Particularly, they have hourglass-like configurations when viewed from above or below.

More particularly, the inner layer 18 is comprised of a substantially fluid-permeable material of any suitable type. The absorbent layer 20 is comprised of a substantially fluid-absorbing material of any suitable type. The outer layer 22 is comprised of a substantially fluid-impermeable material of any suitable type. The materials of the inner, absorbent and outer layers 18, 20, 22 can be the same as those comparable layers found in existing commercially-available diapers. The absorbent layer 20 is generally pad-like in its construction and typically has a thickness which is substantially greater than that of each of the inner and outer layers 18 and 22 and also greater than that of the fluid transport layer 14 as well.

As seen in FIG. 3, the fluid transport layer 14 is disposed between the inner layer 18 and the absorbent layer 20. Alternatively, but probably less desirably, the fluid transport layer 14 could be disposed between the absorbent layer 20 and the outer layer 22. The fluid transport layer 14 also may be incorporated with the inner layer 18 or the absorbent layer 20.

More particularly, the fluid transport layer 14 preferably is in the form of a thin sheet of material and has a main core 14C which includes the peripheral edge 14A and the centrally-located portion 14B spaced inwardly from the peripheral edge 14A. The main core 14C of the layer 14 is comprised of the fluid-permeable chromatographic medium which, when contacted by fluid, draws the fluid via a wicking or capillary action toward the peripheral edge 14A of the layer 14. The chromatographic medium of the main core 14C can be made of any suitable hydrophilic material capable of creating the wicking or capillary action. For instance, the chromatographic medium may be composed of cellulose paper, hydrophilic polyester, nitrocellulose, rayon fiber, nylon fiber, silica gel, filter paper or the like. The main core 14C has an area which includes the area of the centrally-located portion 14B and is substantially greater than the area of the peripheral edge 14A.

The peripheral edge 14A of the fluid transport layer 14 is comprised of or contains any material or reagent or the like which is capable of eliciting a visible change, such as a color change, or the like in response in the presence of fluid, such as urine or the like, on the peripheral edge 14A. The peripheral edge 14A may be a separate entity from the main core 14C which is attached to the main core 14C or the peripheral edge 14A and main core 14C may be a common entity and thus integral parts of the sheet of material of the layer 14. The peripheral edge 14A of the layer 14 can be impregnated with the color change material. In the first embodiment, the peripheral edge 14A which contains the wetness indicator 16 preferably is continuous around the main core 14C of the layer 14, as seen in FIG. 2, and is exposed and visible along the ends and sides of the peripheral edge 12A of the diaper substrate 12 such that the peripheral edge 14A both lines and protrudes from the perimeter or peripheral edge 12A of the diaper substrate 12 of the diaper 10. Thus, the visible response of the wetness indicator 16 can be visible along substantially all portions of the peripheral edge 12A of the diaper substrate 12. The color change or like response of the material of the peripheral edge 14A can be elicited by wetness, pH, temperature, specific gravity, calcium, sodium, chloride, protein, glucose, creatinine, lactate, phosphate, sulfate, uric acid, amino acids, paraminohippuric acid, ketone bodies, bilirubin, nitrite, pKa, albumin or any antibody or reagent specific to biological metabolites or hormones. By way of example, litmus paper could be used as a urinary indicator testing for pH. The colors of the material on the peripheral edge 14A of the layer 14 before and after the material becomes wet may be of any suitable type.

In operation, the diaper 10 is worn by a user, such as a small child (not shown). The wearer of the diaper 10 may urinate onto the inner layer 18 of the diaper 10. The fluid passes onto and through the inner layer 18 and onto the fluid transport layer 14 where most of the fluid then passes through the layer 14 into the absorbent layer 20 where the fluid is collected. The outer layer 22 prevents passage of the fluid beyond the absorbent layer 20. A minimal quantity of the fluid is also drawn along the layer 14 from a point within the centrally-located portion 14B of the main core 14C to the peripheral edge 14A of the fluid transport layer 14. When the fluid contacts the peripheral edge 14A of the layer 14 at any point thereof, the color of the material of the peripheral edge 14A changes providing a visible response. This change in the color of the material of the peripheral edge 14A provides an immediate indicator visible to the person caring for the small child that the child has excreted waste and soiled the diaper and that the diaper 10 should now be replaced with a fresh one.

Figure 5:
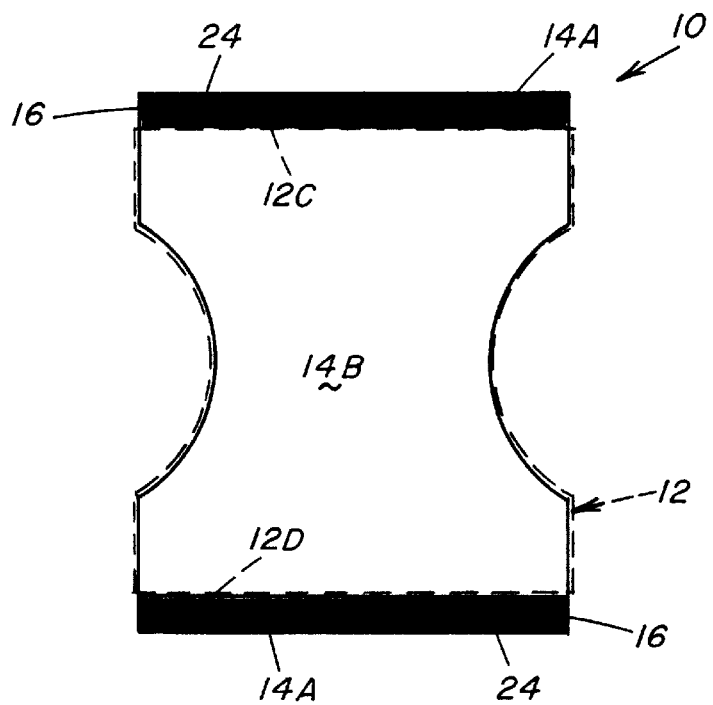
FIG. 5 is a plan view of the diaper of FIG. 5 but shown in a wet condition.

Referring to FIGS. 4 and 5, there is illustrated a second embodiment of the diaper 10 of the present invention shown respectively in dry and wet conditions. In this second embodiment, the visible response of the wetness indicator 16 is a change in the size of a mark 24 applied on the peripheral edge 14A of the fluid transport layer 14. The mark 24 can be an ink substance applied in the form of a line on a first portion of the peripheral edge 14A of the fluid transport layer 14. In response to the presence of fluid, the mark 24 is capable of expanding to cover a second portion of the peripheral edge 14A of the transport layer 14 which is larger than the first portion. Also, the peripheral edge 14A of the transport layer 14 containing the wetness indicator 16 is exposed along at least one or both of the opposite front and rear portions 12C, 12D of the diaper substrate such that the visible response of the wetness indicator 16 can be visible along the at least one or both of the opposite front and rear portions 12C, 12D of the peripheral edge 12A of the diaper substrate 12.

Figure 6:
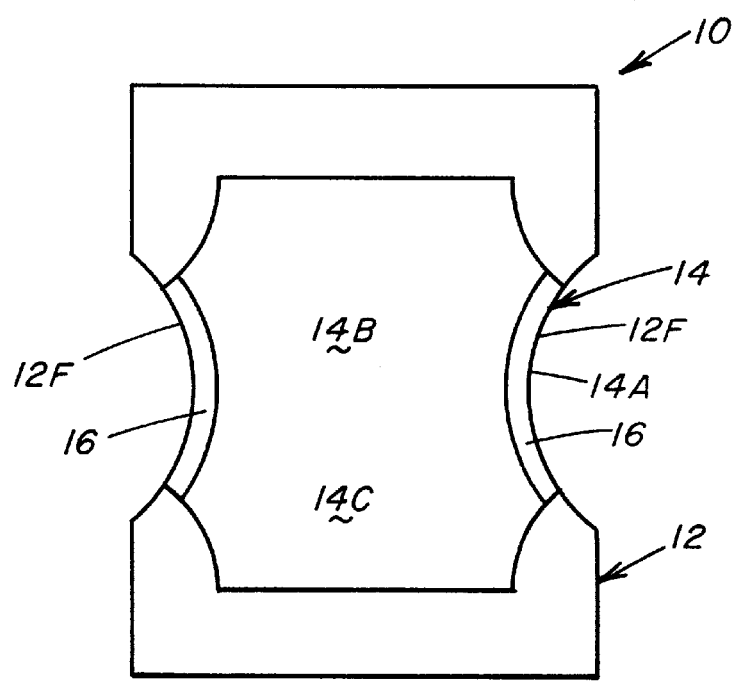
FIG. 6 is a plan view of a third embodiment of the diaper of the present invention.

Referring to FIG. 6, there is illustrated a third embodiment of the diaper 10 of the present invention. In the third embodiment, the peripheral edge 14A of the fluid transport layer 14 containing the wetness indicator 16 is exposed along at least one or both of opposite side portions 12E, 12F of the diaper substrate 12. Thus, the visible response of the wetness indicator 16 can be visible along the at least one or both of the opposite side portions 12E, 12F of the peripheral edge 12A of the diaper substrate 12.

Figure 7:
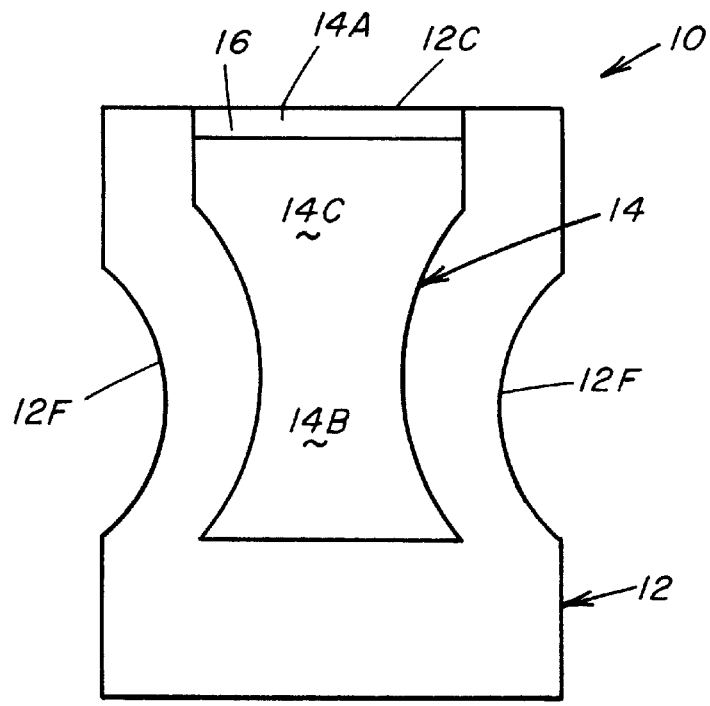
FIG. 7 is a plan view of a fourth embodiment of the diaper of the present invention.

Referring to FIG. 7, there is illustrated a fourth embodiment of the diaper 10 of the present invention. In the fourth embodiment, the transport layer 14 is smaller in area than in the other embodiments such that except for only a portion, such as a front end 14D, thereof the peripheral edge 14B of the layer 14 is spaced inwardly from the peripheral edge 12A of the diaper substrate 12. The wetness indicator 16 is provided on and exposed and extends only along a portion of the peripheral edge 12A of the diaper substrate 12. However, in this embodiment, the transport layer 14 also has the centrally-located portion 14B which is contiguous with the centrally-located region 12B of the diaper substrate 12.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

We claim:

1. A diaper, comprising:
    (a) a diaper substrate having a peripheral edge and a centrally-located region where fluid from a user will make initial contact therewith;
    (b) a fluid transport layer disposed within the diaper substrate and having a peripheral edge and a centrally-located portion disposed at the centrally-located region of the diaper substrate; and
    (c) a wetness indicator on the peripheral edge of the transport layer and exposed and extending along at least a portion of the peripheral edge of the diaper substrate;
    (d) said fluid transport layer being made of a material capable of drawing fluid via capillary action from said centrally-located portion of said layer at said centrally-located region of said diaper substrate toward said peripheral edge of said layer and into contact with said wetness indicator, said wetness indicator being a material capable of eliciting a visible response in the presence of fluid.

2. The diaper of claim 1 wherein said diaper substrate includes:
    an inner layer of a substantially fluid-permeable material; and
    an absorbent layer of a substantially fluid-absorbing material; and
    an outer layer of a substantially fluid-impermeable material.

3. The diaper of claim 1 wherein said diaper substrate includes:
    an inner layer of a substantially fluid-permeable material; and
    an absorbent layer of a substantially fluid-absorbing material disposed outwardly of said inner layer.

4. The diaper of claim 1 wherein said diaper substrate includes:
    an absorbent layer of a substantially fluid-absorbing material; and
    an outer layer of a substantially fluid-impermeable material disposed outwardly of said absorbent layer.

5. The diaper of claim 1 wherein said fluid transport layer is a fluid-permeable chromatographic medium.

6. The diaper of claim 1 wherein said visible response of said wetness indicator is a color change.

7. The diaper of claim 1 wherein said visible response of said wetness indicator is a change in the size of a mark on said peripheral edge of said fluid transport layer.

8. The diaper of claim 1 wherein said peripheral edge of said fluid transport layer containing said wetness indicator is exposed continuously around said diaper substrate such that said response of said wetness indicator can be visible along substantially all portions of said peripheral edge of said diaper substrate.

9. The diaper of claim 1 wherein said peripheral edge of said fluid transport layer containing said wetness indicator is exposed along at least one of opposite side portions of said diaper substrate such that said response of said wetness indicator can be visible along said one of said opposite side portions of said peripheral edge of said diaper substrate.

10. The diaper of claim 1 wherein said peripheral edge of said fluid transport layer containing said wetness indicator is exposed along both of opposite side portions of said diaper substrate such that said response of said wetness indicator can be visible along both of said opposite side portions of said peripheral edge of said diaper substrate.

11. The diaper of claim 1 wherein said peripheral edge of said fluid transport layer containing said wetness indicator is exposed along at least one of said opposite front and rear portions of said diaper substrate such that said response of said wetness indicator can be visible along said one of said opposite front and rear portions of said peripheral edge of said diaper substrate.

12. The diaper of claim 1 wherein said peripheral edge of said fluid transport layer containing said wetness indicator is exposed along both of opposite front and rear portions of said diaper substrate such that said response of said wetness indicator can be visible along both of said opposite front and rear portions of said peripheral edge of said diaper substrate.

13. The diaper of claim 2 wherein said absorbent layer is pad-like in construction and has a thickness which is substantially greater than that of each of said inner and outer layers and also greater than that of said fluid transport layer.

14. The diaper of claim 3 wherein said fluid transport layer is disposed between said inner layer and said absorbent layer.

15. The diaper of claim 3 wherein said fluid transport layer is incorporated with said inner layer.

16. The diaper of claim 3 wherein said fluid transport layer is incorporated with said absorbent layer.

17. The diaper of claim 4 wherein said fluid transport layer is disposed between said absorbent layer and said outer layer.

18. The diaper of claim 4 wherein said fluid transport layer is incorporated with said outer layer.

19. The diaper of claim 4 wherein said fluid transport layer is incorporated with said absorbent layer.

20. The diaper of claim 7 wherein said mark is an ink substance applied on a first portion of said peripheral edge of said fluid transport layer and capable of expanding in response to the presence of fluid to cover a second portion of said peripheral edge of said fluid transport layer larger than said first portion.

* * * * *